United States Patent [19]
Chen et al.

[11] Patent Number: 5,468,796
[45] Date of Patent: Nov. 21, 1995

[54] CREPING CHEMICAL COMPOSITION AND METHOD OF USE

[75] Inventors: Franklin M. C. Chen, Appleton; Frank G. Druecke, Oshkosh, both of Wis.

[73] Assignee: Kimberly-Clark Corporation, Neenah, Wis.

[21] Appl. No.: 291,804

[22] Filed: Aug. 17, 1994

[51] Int. Cl.$^6$ .................................................. C08K 5/06
[52] U.S. Cl. ........................ 524/377; 568/616; 568/624; 568/625
[58] Field of Search ............................ 568/616, 624, 568/625; 524/377

[56] References Cited

U.S. PATENT DOCUMENTS

| | | | |
|---|---|---|---|
| 2,426,312 | 8/1947 | Lewis et al. | 19/69 |
| 2,718,142 | 9/1955 | Schwartz et al. | 73/100 |
| 2,978,636 | 4/1961 | Fountain | 324/54 |
| 3,164,015 | 1/1965 | Schafer | 73/159 |
| 3,528,145 | 9/1970 | Troope et al. | 26/63 |
| 3,529,045 | 9/1970 | Rosenstein | 264/40 |
| 3,546,065 | 12/1970 | Ostermeier | 162/111 |
| 3,640,841 | 2/1972 | Winslow et al. | 162/164 |
| 3,650,491 | 3/1972 | Pfeiffer | 242/75.51 |
| 4,053,422 | 10/1977 | Walker | 252/8.5 C |
| 4,076,633 | 2/1978 | Edwards et al. | 252/8.75 |
| 4,308,092 | 12/1981 | Latimer et al. | 162/111 |
| 4,406,737 | 9/1983 | Latimer et al. | 162/111 |
| 4,416,148 | 11/1983 | Klus et al. | 73/64.4 |
| 4,440,898 | 4/1984 | Pomplun et al. | 524/503 |
| 4,501,640 | 2/1985 | Soerens | 162/111 |
| 4,507,429 | 3/1985 | Lenney | 524/800 |
| 4,528,316 | 7/1985 | Soerens | 524/503 |
| 4,632,730 | 12/1986 | Ulubay et al. | 162/111 |
| 4,649,605 | 3/1987 | Neal | 19/106 R |
| 4,663,005 | 5/1987 | Edson | 204/129.85 |
| 4,684,439 | 8/1987 | Soerens | 162/111 |
| 4,720,383 | 1/1988 | Drach et al. | 424/70 |
| 4,788,243 | 11/1988 | Soerens | 524/503 |
| 4,795,530 | 1/1989 | Soerens et al. | 162/111 |
| 4,942,077 | 7/1990 | Wendt et al. | 482/152 |
| 4,981,557 | 1/1991 | Bjorkquist | 162/168.2 |
| 5,135,615 | 8/1992 | Rokman | 162/263 |
| 5,178,676 | 1/1993 | Lackey et al. | 106/287.14 |
| 5,179,150 | 1/1993 | Furman, Jr. et al. | 524/376 |
| 5,187,219 | 2/1993 | Furman, Jr. | 524/377 |
| 5,234,547 | 8/1993 | Knight et al. | 162/111 |
| 5,246,544 | 9/1993 | Hollenberg et al. | 162/111 |
| 5,246,545 | 9/1993 | Ampulski et al. | 162/112 |
| 5,297,062 | 3/1994 | Cresson et al. | 364/564 |

FOREIGN PATENT DOCUMENTS

| | | |
|---|---|---|
| 1067230 | 11/1979 | Canada. |
| 0548959 | 6/1993 | European Pat. Off.. |
| 0110764 | 9/1981 | Japan. |
| 1116392 | 6/1968 | United Kingdom. |

OTHER PUBLICATIONS

Tsai, F. J. and Torkelson, J. M. "Roles of Phase Separation Mechanism and Coarsening in the Formation of Poly(m-ethyl methacrylate) Asymmetric Membranes", *Marcomolecules*, 1990, 23,775.

SensaDyne® 6000 Surface Tensionmeter Bulletin, published by Chem–Dyne Research Corp, Date Unknown.

*Primary Examiner*—Edward Cain
*Attorney, Agent, or Firm*—Gregory E. Croft

[57] ABSTRACT

In the manufacture of soft tissue products such as facial and bath tissue, a creping adhesive composition comprising from about 0.05 to about 20 dry weight percent of an ethoxylated acetylenic diol has been found to reduce skulch, improve creping blade life, and improve crepe quality. The creping adhesive composition is particularly useful for creping throughdried tissue webs.

32 Claims, No Drawings

CREPING CHEMICAL COMPOSITION AND METHOD OF USE

BACKGROUND OF THE INVENTION

In the manufacture of soft tissues and related paper products such as facial tissue, bath tissue, kitchen towels and dinner napkins, aqueous suspensions of papermaking fibers are deposited onto a forming fabric to form an embryonic web. The embryonic web is dewatered, dried and thereafter creped to soften the resulting sheet. In carrying out the creping step, a creping adhesive is typically sprayed onto the surface of a rotating creping cylinder, such as a Yankee dryer, to help build an adhesive (dryer) coating to which the tissue sheet is adhered. The adhered tissue is dislodged from the surface of the creping cylinder by contact with a doctor blade. Crepe quality is maintained by regularly changing the doctor blades in order to maintain a uniform dryer coating, which becomes uneven due to skulch formation on the dryer surface. A non-uniform dryer coating is one of the major reasons for very frequent doctor blade changes. Blade life may be as short as 30 minutes in some instances. Necessary and frequent blade changes contribute to waste and delay and are also an expense to be minimized.

Hence there is a need for improved creping methods which are more economical and provide more consistent quality.

SUMMARY OF THE INVENTION

It has now been discovered that tissue quality and creping blade life can both be improved by incorporating a particular class of surfactants into the creping adhesive formulation. The creping adhesive formulations of this invention are particularly useful for use in throughdrying tissue making processes where skulch formation can be a significant problem, although wet pressing processes can also benefit from their use. While not being bound to any particular theory, it is believed that a particular class of surfactants, when added to an aqueous creping adhesive mixture, reduces the dynamic surface tension more effectively than other classes of surfactants. When the dynamic surface tension of a creping adhesive mixture is reduced to about 40 dynes per centimeter or less, the uniformity of the dryer coating is maintained for a longer period of operation before a doctor blade change is necessary.

Hence in one aspect, the invention resides in a creping adhesive composition comprising an ethoxylated acetylenic diol having the formula:

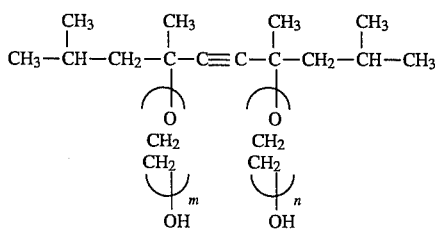

wherein m+n=the number of moles of ethylene oxide, which can be from about 1 to about 10, more specifically from about 1 to about 5, and still more specifically from about 1 to about 3.

It has been found that by incorporating an ethoxylated acetylenic diol into a creping adhesive composition, improvements can be achieved in terms of crepe quality and doctor blade life. Whereas conventional commercial creping adhesives typically produce less than about 100,000 yards of tissue between creping blade changes, creping adhesives in accordance with this invention can produce about 150,000 yards or more. Such creping adhesive compositions have a dynamic surface tension of about 40 dynes per centimeter or less, as measured by the maximum bubble pressure method, measured at 5 bubbles per second using an aqueous creping adhesive mixture having a solids content of 8–12 percent, wherein 10 percent of the solids is the surfactant. The maximum bubble pressure method of measuring dynamic surface tension is well known in the art, as described in Arthur Adamson's book "Physical Chemistry of Surfaces" (1982) and in U.S. Pat. No. 4,416,148 entitled "Surface Tensiometer", issued on Nov. 22, 1983 to John P. Klus et al., both of which are herein incorporated by reference. Suitable commercially available ethoxylated acetylenic diols include Surfynol 420, Surfynol 465 and Surfynol 504, available from Air Products Company, Allentown, Pa.

More specifically, the creping adhesive formulation preferably comprises a semi-crystalline polymer, a polyamide or sorbitol, and a release agent. The ethoxylated acetylenic diol acts as the release agent or a component thereof. The amount of the ethoxylated acetylenic diol in the creping adhesive composition can be from about 0.05 to about 20 dry weight percent, more specifically from about 1 to about 10 dry weight percent, and still more specifically from about 1 to about 3 dry weight percent. As used herein, "dry weight percent" refers to a percentage based solely on the amount of solids present in the composition.

Suitable semi-crystalline polymers include polyvinyl alcohol, polyvinylpyrrolidone, hydroxyethylcellulose, carboxymethylcellulose, microcrystalline cellulose, and the like. The amount of the crystalline polymer component, if present, can be from about 50 to about 90 dry weight percent of the creping adhesive composition.

Suitable polyamides possess an intrinsic viscosity of from about 10 to about 200 cubic centimeters per gram and, if present, can be from about 10 to about 50 dry weight percent of the creping adhesive composition. Specific polyamides include Crepeplus 97, available from Betz Paper Chemical Co., Jacksonville, Fla., and Creptrol 190, available from Hercules, Inc., Wilmington, Del.

The amount of the release agent can be from about 0.05 to about 20 dry weight percent of the creping adhesive composition and preferably further comprises a cationic oligomer in the amount of from about 5 to about 95 weight percent of the amount of the release agent. Suitable cationic oligomers include quaternary amines, such as Quaker 2008, available from Quaker Chemical Company, Conshohocken, Pa.

In another aspect, the invention resides in a method of making a creped tissue comprising the steps of: (a) depositing an aqueous suspension of papermaking fibers onto a forming fabric to form an embryonic web; dewatering and drying the embryonic web to form a tissue web; (c) applying a creping adhesive to the surface of a creping cylinder; (d) adhering the tissue web to the creping cylinder; and (e) dislodging th tissue web from the creping cylinder with a doctor blade to form a soft tissue sheet, wherein the creping adhesive comprises from about 0.05 to about 20 dry weight percent of the creping adhesive referred to above. The creping adhesive is suitably an aqueous suspension containing from about 0.1 to about 10 weight percent solids, more specifically from about 0.5 to about 2 weight percent solids, and still more specifically about 1 percent solids. The rate at which the creping adhesive is applied to the surface of the creping cylinder can be from about 2 to about 20 pounds per ton of fiber.

EXAMPLES

Example 1.

To compare the efficiency of lowering the dynamic surface tension of different surfactants, 18 chemical stock solutions or formulations having three components as shown in Table 1 were made for comparison to a control (No. 17). The chemical stocks for formulations 1–17 were diluted to 1 percent solids solutions before being subjected to dynamic surface tension measurements in accordance with the aforementioned maximum bubble pressure method. The chemical stocks for formulations 18 and 19 were diluted to 8.9 percent solids solutions before being measured for dynamic surface tension.

TABLE 1

CHEMICAL STOCK SOLUTIONS FOR DYNAMIC SURFACE TENSION MEASUREMENTS

| Form | Chem #1 | % Chem #1 | Chem #2 | % Chem #2 | Chem #3 | % Chem #3 | Chem #4 | % Chem #4 | Surface Tension |
|---|---|---|---|---|---|---|---|---|---|
| 1 | PVOH | 60.00 | Sorbitol | 38.00 | Triton X100 | 2.00 | — | — | 52.8 |
| 2 | PVOH | 40.00 | Sorbitol | 58.00 | Triton X100 | 2.00 | — | — | 52.0 |
| 3 | PVOH | 60.00 | Sorbitol | 38.00 | Surfynol 420 | 2.00 | — | — | 44.2 |
| 4 | PVOH | 40.00 | Sorbitol | 58.00 | Surfynol 420 | 2.00 | — | — | 48.6 |
| 5 | PVOH | 60.00 | Sorbitol | 38.00 | Aerosol OT | 2.00 | — | — | 50.6 |
| 6 | PVOH | 40.00 | Sorbitol | 58.00 | Aerosol OT | 2.00 | — | — | 52.0 |
| 7 | PVOH | 60.00 | Sorbitol | 38.00 | Quaker 2008 | 2.00 | — | — | 62.2 |
| 8 | PVOH | 40.00 | Sorbitol | 58.00 | Quaker 2008 | 2.00 | — | — | 62.6 |
| 9 | PVOH | 80.00 | Creptrol 190 | 18.00 | Triton xlOO | 2.00 | — | — | 53.7 |
| 10 | PVOH | 80.00 | Creptrol 190 | 18.00 | Surfynol 420 | 2.00 | — | — | 47.8 |
| 11 | PVOH | 80.00 | Creptrol 190 | 18.00 | Aeasol OT | 2.00 | — | — | 61.5 |
| 12 | PVOH | 80.00 | Creptrol 190 | 18.00 | Quaker 2008 | 2.00 | — | — | 62.2 |
| 13 | PVOH | 48.00 | Crepeplus 97 | 50.00 | Triton X100 | 2.00 | — | — | 56.0 |
| 14 | PVOH | 48.00 | Crepeplus 97 | 50.00 | Surfynol 420 | 2.00 | — | — | 48.1 |
| 15 | PVOH | 48.00 | Crepeplus 97 | 50.00 | Aerosol OT | 2.00 | — | — | 61.9 |
| 16 | PVOH | 48.00 | Crepeplus 97 | 50.00 | Quaker 2008 | 2.00 | — | — | 64.1 |
| 17 | PVOH | 60.00 | Sorbitol | 40.00 | — | — | — | — | 63.9 |
| 18 | PVOH | 40.00 | Sorbitol | 29.00 | Quaker 2008 | 1.00 | Surfynol 504 | 10.00 | 33.7 |
| 19 | PVOH | 40.00 | Sorbitol | 29.00 | Quaker 2008 | 1.00 | Triton X-100 | 10.00 | 47.1 |

The resulting dynamic surface tensions indicate that the ethoxylated acetylenic diol surfactant (Surfynol 420) was more efficient in lowering the dynamic surface tension than other surfactants such as Triton X-100 or Aerosol TO.

Stock solutions 18 and 19 were prepared to see the effect of the combination of Quaker 2008 and other surfactants such as Surfynol 504 and Triton X-100. These two chemical stock solutions had a solid content of 8.9%. The results indicate that a combination of Quaker 2008 and Surfynol 504 is more effective in lowering the dynamic surface tension than the combination of Quaker 2008 and Triton X-100.

Example 2.

In order to illustrate the benefit of reducing skulch in throughdrying operations, a high speed trial (3000–5000 feet per minute) was conducted during the manufacture of bath tissue at a rate of 0.16 tons per minute. The creping adhesive was sprayed onto the surface of the creping cylinder at an add-on of 12.51 pounds per ton of fiber. The creping adhesive formulation was applied at the following rates: polyvinylalcohol, 525.3 grams per minute; Crepeplus 97, 135.45 grams per minute; and Quaker 2008, 6.00 grams per minute. Using this creping adhesive formulation, skulch formation was common. Then 33.99 grams per minute of Surfynol 504 was added to the creping adhesive formulation. Within about 2–10 minutes, the skulch on the dryer disappeared, illustrating the effectiveness of the Surfynol 504.

Example 3.

In order to further illustrate the benefits of the creping adhesive formulations of this invention, additional continuous trials were conducted on a tissue machine producing bath tissue at a speed of about 3200 feet per minute. The trial matrix is shown in Table 2. The crepe quality was observed and evaluated on a scale of 1 to 4, with grade 1 being the best. Observations were also noted regarding creping blade life.

TABLE 2

CREPING FORMULATION CELLS

Ingredient Flow Rate (gm/min)

| Cell | PVA | Sorbitol | Crepeplus #97 | Quaker 2008 | Surfynol #504 | Comments |
|---|---|---|---|---|---|---|
| 1 | 51.00 | 8.40 | | 3.00 | | Control |
| 2 | 51.00 | 8.40 | | 0.30 | 2.72 | Unstable web |
| 3 | 51.00 | 8.40 | | 0.23 | 2.04 | Same as #2 |
| 4 | 51.00 | 8.40 | | | 2.05 | Unacceptable creping Skutch at 1st roll |
| 5 | 51.00 | 8.40 | | | 2.72 | Same as #4 |
| 6 | 51.00 | | 4.56 | 3.00 | | Excellent Crepe 3 rolls/blade |
| 7 | 51.00 | | 4.56 | 2.63 | | Same as #6 |
| 8 | 51.00 | | 5.00 | 0.30 | 2.72 | Same as |

TABLE 2-continued

CREPING FORMULATION CELLS

Ingredient Flow Rate (gm/min)

| Cell | PVA | Sorbitol | Crepeplus #97 | Quaker 2008 | Surfynol #504 | Comments |
|------|-------|----------|---------------|-------------|---------------|----------|
| 9 | 51.00 | | 4.56 | 0.45 | 4.08 | #6 Excellent crepe Excellent blade life |

Referring to Table 2, the best formulation was Cell #9. The creping quality was grade 1 up to the 12th roll using only one single blade. This formulation was repeated at a later date and was run for three hours with the same blade. Every roll produced had a crepe quality of grade 1. By comparison, an adhesive formulation consisting of polyvinyl alcohol, Sorbitol and Quaker 2008 run for two hours and fifty-five minutes ended up with a crepe quality of grade 3.

It will be appreciated that the foregoing examples, given for purposes of illustration, are not to be construed as limiting the scope of this invention, which is defined by the following claims and all equivalents thereto.

We claim:

1. A creping adhesive comprising a cationic oligomer and from about 0.05 to about 20 dry weight percent of an ethoxylated acetylenic diol having the formula:

$$CH_3-CH(CH_3)-CH_2-C(CH_3)(O-(CH_2CH_2O)_m-H)-C\equiv C-C(CH_3)(O-(CH_2CH_2O)_n-H)-CH_2-CH(CH_3)-CH_3$$

wherein the sum of m+n is from about 1 to about 10, and wherein the amount of the cationic oligomer is from about 5 to about 95 weight percent of the amount of the ethoxylated acetylenic diol.

2. The creping adhesive of claim 1 wherein the amount of the ethoxylated acetylenic diol is from about 1 to about 10 dry weight percent.

3. The creping adhesive of claim 1 wherein the amount of the ethoxylated acetylenic diol is from about 1 to about 3 dry weight percent.

4. The creping adhesive of claim 1 wherein the cationic oligomer is a quaternary amine.

5. The creping adhesive of claim 1 further comprising from about 10 to about 50 dry weight percent of a polyamide having an intrinsic viscosity of from about 10 to about 200 cubic centimeters per gram.

6. The creping adhesive of claim 1 further comprising from about 50 to about 90 dry weight percent of a film forming semicrystalline polymer.

7. The creping adhesive of claim 6 wherein the semicrystalline polymer is polyvinyl alcohol.

8. The creping adhesive of claim 6 wherein the semicrystalline polymer is selected from the group consisting of polyvinylpyrrolidone, hydroxyethylcellulose, carboxymethylcellulose, and microcrystalline cellulose.

9. A creping adhesive comprising from about 50 to about 90 dry weight percent of a semicrystalline polymer selected from the group consisting of polyvinyl alcohol and polyvinylpyrrolidone, from about 10 to about 50 dry weight percent of a polyamide having an intrinsic viscosity of from about 10 to about 200 cubic centimeters per gram, and from about 1 to about 20 dry weight percent of a release agent comprising from about 5 to about 95 dry weight percent of an ethoxylated acetylenic diol of the formula:

$$CH_3-CH(CH_3)-CH_2-C(CH_3)(O-(CH_2CH_2O)_m-H)-C\equiv C-C(CH_3)(O-(CH_2CH_2O)_n-H)-CH_2-CH(CH_3)-CH_3$$

wherein the sum of m+n is from about 1 to about 5, said creping adhesive having a cloud point of about 60 or less and a dynamic surface tension of about 40 dynes per centimeter or less.

10. The creping adhesive of claim 9, wherein the release agent further comprises from about 5 to about 95 dry weight percent of a cationic oligomer.

11. The creping adhesive of claim 10 wherein the cationic oligomer is a quaternary amine.

12. An aqueous creping adhesive composition comprising from about 0.1 to about 10 weight percent solids, said composition having a dynamic surface tension of about 40 dynes per centimeter or less.

13. A creping adhesive composition comprising from about 10 to about 50 dry weight percent of a polyamide having an intrinsic viscosity of from about 10 to about 200 cubic centimeters per gram and from about 0.05 to about 20 dry weight percent of an ethoxylated acetylenic diol having the formula:

$$CH_3-CH(CH_3)-CH_2-C(CH_3)(O-(CH_2CH_2O)_m-H)-C\equiv C-C(CH_3)(O-(CH_2CH_2O)_n-H)-CH_2-CH(CH_3)-CH_3$$

wherein the sum of m+n is from about 1 to about 10.

14. The creping composition of claim 13 wherein the amount of the ethoxylated acetylenic diol is from about 1 to about 10 dry weight percent.

15. The creping composition of claim 13 wherein the amount of the ethoxylated acetylenic diol is from about 1 to about 3 dry weight percent.

16. The creping adhesive composition of claim 13 further comprising from about 50 to about 90 dry weight percent of a film forming semicrystalline polymer.

17. The creping adhesive composition of claim 16 wherein the semicrystalline polymer is polyvinyl alcohol.

18. The creping adhesive composition of claim 16 wherein the semicrystalline polymer is selected from the group consisting of polyvinylpyrrolidone, hydroxyethylcellulose, carboxymethylcellulose, and microcrystalline cellulose.

19. A creping adhesive composition comprising from about 50 to about 90 dry weight percent of a film forming semicrystalline polymer and from about 0.05 to about 20 dry weight percent of an ethoxylated acetylenic diol having the formula:

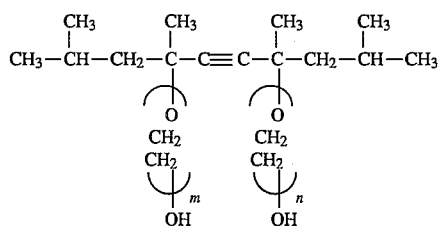

wherein the sum of m+n is from about 1 to about 10.

20. The creping adhesive composition of claim 19 wherein the amount of the ethoxylated acetylenic diol is from about 1 to about 10 dry weight percent.

21. The creping adhesive composition of claim 19 wherein the amount of the ethoxylated acetylenic diol is from about 1 to about 3 dry weight percent.

22. The creping adhesive composition of claim 19 wherein the semicrystalline polymer is polyvinyl alcohol.

23. The creping adhesive composition of claim 19 wherein the semicrystalline polymer is selected from the group consisting of polyvinylpyrrolidone, hydroxyethylcellulose, carboxymethylcellulose, and microcrystalline cellulose.

24. A creping adhesive composition comprising from about 0.1 to about 10 weight percent solids and from about 0.05 to about 20 dry weight percent of an ethoxylated acetylenic diol having the formula:

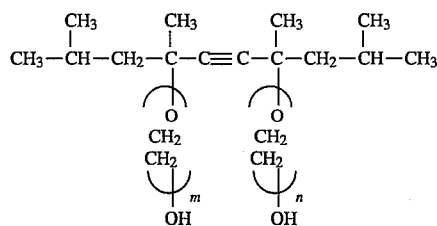

wherein the sum of m+n is from about 1 to about 10, said composition having a dynamic surface tension of about 40 dynes per centimeter or less.

25. The creping adhesive of claim 24 wherein the amount of the ethoxylated acetylenic diol is from about 1 to about 10 dry weight percent.

26. The creping adhesive of claim 24 wherein the amount of the ethoxylated acetylenic diol is from about 1 to about 3 dry weight percent.

27. The creping adhesive of claim 24 further comprising a cationic oligomer in an amount of from about 5 to about 95 weight percent of the amount of the ethoxylated acetylonic diol.

28. The creping adhesive of claim 24 wherein the cationic oligomer is a quaternary amine.

29. The creping adhesive of claim 24 further comprising from about 10 to about 50 dry weight percent of a polyamide having an intrinsic viscosity of from about 10 to about 200 cubic centimeters per gram.

30. The creping adhesive of claim 24 further comprising from about 50 to about 90 dry weight percent of a film forming semicrystalline polymer.

31. The creping adhesive of claim 24 wherein the semicrystalline polymer is polyvinyl alcohol.

32. The creping adhesive of claim 24 wherein the semicrystalline polymer is selected from the group consisting of polyvinylpyrrolidone, hydroxyethylcellulose, carboxymethylcellulose, and microcrystalline cellulose.

\* \* \* \* \*